(12) United States Patent
Victor

(10) Patent No.: US 9,011,442 B2
(45) Date of Patent: Apr. 21, 2015

(54) DISPOSABLE SURGICAL HEMISPHERICAL CUTTER FOR CONVEX AND CONCAVE SURFACES

(75) Inventor: Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 172 days.

(21) Appl. No.: 13/355,973

(22) Filed: Jan. 23, 2012

(65) Prior Publication Data
US 2012/0191098 A1    Jul. 26, 2012

Related U.S. Application Data

(60) Provisional application No. 61/434,839, filed on Jan. 21, 2011.

(51) Int. Cl.
*A61B 17/16* (2006.01)
*A61B 17/00* (2006.01)

(52) U.S. Cl.
CPC ..... *A61B 17/1666* (2013.01); *A61B 2017/0023* (2013.01)

(58) Field of Classification Search
USPC ............. 606/79–81, 85, 86 R, 167, 180
See application file for complete search history.

(56) References Cited

U.S. PATENT DOCUMENTS

| | | | |
|---|---|---|---|
| 3,630,204 A * | 12/1971 | Fishbein | .................. 606/81 |
| 3,633,583 A * | 1/1972 | Fishbein | .................. 606/81 |
| 4,131,116 A | 12/1978 | Hedrick | |
| 4,621,637 A | 11/1986 | Fishbein | |
| 4,811,632 A | 3/1989 | Salyer | |
| 5,116,165 A | 5/1992 | Salyer | |
| 5,203,653 A | 4/1993 | Kudla | |
| 5,376,092 A | 12/1994 | Hein et al. | |
| 5,658,290 A | 8/1997 | Lechot | |
| 5,755,719 A | 5/1998 | Frieze et al. | |
| 5,897,558 A | 4/1999 | Frieze et al. | |
| 6,258,093 B1 | 7/2001 | Edwards et al. | |
| 6,764,490 B1 | 7/2004 | Szabo | |
| 7,559,928 B2 * | 7/2009 | Johnson et al. | ............. 606/81 |
| 7,588,572 B2 | 9/2009 | White et al. | |
| 7,837,686 B1 | 11/2010 | Tulkis | |

(Continued)

FOREIGN PATENT DOCUMENTS

WO    2007049113    5/2007

OTHER PUBLICATIONS

Patent search results.
(Continued)

*Primary Examiner* — Nicholas Woodall
*Assistant Examiner* — Larry E Waggle, Jr.
(74) *Attorney, Agent, or Firm* — Michael F. Scalise

(57) ABSTRACT

A disposable reamer designed to improve bone and tissue removal efficiency is described. The reamer device comprises a reamer body shell, a series of reamer blades and a reamer shaft interface. The reamer body shell has a hemispherical structure having a concave interior surface and a convex outer surface. The series of reamer blades have a cutting portion comprised of a series of discrete cutting edges that is bent at an angle from the planar portion of the blade. The reamer blades are positioned along the curved concave interior surface of the hemispherical shell or along the curved convex outer surface of the shell. The reamer blades are positioned along the hemispherical shell such that their leading edges lie parallel to and tangent a bisecting plane.

41 Claims, 11 Drawing Sheets

(56) References Cited

U.S. PATENT DOCUMENTS

| | | | |
|---|---|---|---|
| 8,366,713 B2 | 2/2013 | Long et al. | |
| 8,407,880 B2 * | 4/2013 | Stamp | 29/527.4 |
| 8,435,243 B2 | 5/2013 | White et al. | |
| 8,460,298 B2 * | 6/2013 | O'Donoghue | 606/80 |
| 2009/0078096 A1 | 3/2009 | Ryall et al. | |
| 2010/0069908 A1 | 3/2010 | Sidebotham et al. | |

OTHER PUBLICATIONS

European Search Report 2 47852 A1 dated Jul. 25, 2012.

\* cited by examiner

DISPOSABLE SURGICAL HEMISPHERICAL CUTTER FOR CONVEX AND CONCAVE SURFACES

CROSS-REFERENCE TO RELATED APPLICATIONS

This application claims priority from U.S. Provisional Patent Application Ser. No. 61/434,839, filed Jan. 21, 2011.

FIELD OF THE INVENTION

The present invention relates to the art of orthopedic reamers, and more particularly, to a disposable reamer used for cutting a concave or convex surface of a bone.

PRIOR ART

Reamers are tools used in orthopedic procedures to cut bone and associated tissue matter. In particular, the present invention is focused on disposable cutting tools for orthopedic surgical applications. Specifically, the present invention is utilized to preferably cut hemispherical surfaces of bone and/or tissue matter. Bones that require an exterior rounding of a convex hemispherical surface, typically include the femur or the ends of the phalanges of the hand or foot. Such a reaming process is often rendered following arthroplasty, which typically results from the condition of rheumatoid arthritis.

An example of producing a concave hemispherical surface includes reshaping of the acetabulum of the pelvis. In a surgical procedure, the acetabulum is reshaped to accept a cup prosthesis during hip arthroplasty. That is following the destruction of cartilage and bone, generally due to arthritis.

Most prior art acetabular reamers used in surgeries are of the geometry stated in U.S. Pat. No. 4,811,632 to Salyer. The reamer disclosed in the '632 patent has a hemispherical shell with a plurality of perforated holes that act as cutting edges. Each hole is surrounded by a margin of the hemispherical shell. A portion of the margin of the shell is generally deformed outwardly to form the cutting edge raised above the surface of the shell. This type of prior art reamer requires complex manufacturing methods and costly materials to produce, therefore necessitating that the device be reused multiple times. In the case of cup arthroplasty in either a hip replacement or hip revision surgery, a set of acetabular reamers may consist of reamers with diameters ranging from about 37 mm to about 68 mm in 1 mm step increments, thus totaling over 30 sizes. Over time, as these reamers are used and reused, the cutting blades become dull. Therefore, the reamer cutting blades are required to be resharpened and sterilized before each reuse. However, this resharpening and sterilization process adds additional cost and increases the possibility of infection. There is a high likelihood that the sterilization process may not remove all possible infection agents such as bacteria, machining lubricants, and the like.

The geometry of the cutting edges also are known to affect the efficiency of the cutting tool. Preferably, the cutting edge of any surgical tool should be able to cut through a wide variety of tissue and bone. Examples of tissue and bone include cartilage, muscle and bone material ranging from porous cancellous bone to denser, harder cortical bone. Surgical to which merely scrape or "tear off" tissue work well on hard bone but tend to be less effective with less dense porous bone. Such scraping instruments are described in U.S. Pat. Nos. 3,630,204 and 3,633,583, both to Fishbein. In U.S. Pat. No. 3,630,204, Fishbein describes a bone cutting tool blade that is rotatable about an axis wherein the axis intersects the cutting blade at the cutting edge midpoint. At this intersection, the cutting edge reverses orientation to accommodate approaching bone and tissue that is being cut. The cutting edge is segmented to reduce the amount of contact with the surface being cut, thus reducing the cutting forces on the blade. The cutting segments on one side of the midpoint correspond with gaps or notches on the opposite side of the mipoint, thus allowing the cutting edge of the blade to contact a full hemispherical surface when rotated about the axis.

In U.S. Pat. No. 3,633,583, Fishbein describes a surgical device incorporating cutting blades similar to the construction of the blade described in the '204 patent. The blades disclosed in the '583 patent, however, do not have notches as specified in the '204 patent. Instead, the blades are positioned on the tool such that their cutting edges lie within a plane that includes the axis of rotation of the device. Thus, the geometry, position and construction of the cutting edge of the blades of the tools described in the Fishbein '204 and '583 patents are mainly suited for a scraping method of tissue and bone removal. The Fishbein blades, however, are not capable of efficient cutting of bone and/or tissue.

In U.S. Pat. No. 4,621,637 to Fishbein, an attempt is made to address the scraping method of tissue and bone removal. In the '637 patent, Fishbein incorporates a blade where the underside of the cutting surface is ground to effectively produce a cutting edge with a positive, non-zero rake angle. The geometry of this cutting edge insures that a skiving or cutting method of tissue and bone removal is employed. The blades of the '637 patent are designed such that they are separate from the shell. Fishbein contends that this particular design yields a more cost effective method of manufacture when the cutting edge is incorporated within the shell. However, such a design does not produce a reamer with the cutting efficies afforded to by the present invention.

Such is also the case with U.S. Pat. No. 4,131,116 to Hedrick for creating a concave hemispherical shape. Hedrich incorporates radial slots in a formed hemispherical shell where the trailing edge of each radial slot is formed as a cutting edge and raised slightly above the surface of the hemispherical shell. Salyer also utilizes radial slots formed in a hemispherical shell in U.S. Pat. No. 5,116,165. However, Salyer's reamer design is different than Hendrick's in that Salyer utilizes radial slots that are shorter in length than those described in U.S. Pat. No. 4,131,116. In addition, the Salyer radial slots are positioned over the surface of the shell in a spiral arrangement. In the '116 patent, Hendrick contends that the position of the cutting edges parallel to the hemispherical shell produce a more precise cut. Additionally, the short lengths of the slots in the '116 patent are claimed to reduce chipping and produce a more desirable cut surface finish.

Finally, U.S. Pat. No. 5,203,653 to Kudla, U.S. Pat. No. 5,376,092 to Hein and Utley and U.S. Pat. No. 6,764,490 to Szabo all make use of a formed shell with helical slots cut into the shell in which the trailing edge of the slots serve as the cutting edge. In all cases, the method of incorporating the cutting edge into the hemispherical shell requires the use of costly materials and manufacturing methods. The present invention, unlike the prior art, incorporates a series of discrete cutting teeth with cutting edges that are strategically positioned at an offset distance. The position of these discrete cutting teeth in the design of the present invention, produces a reamer with increased cutting efficiencies in comparison to those of the prior art. Such increases in cutting efficiency minimizes drive motor torque, which allows for increased cutting precision and minimized patient trauma.

Accordingly, the present invention provides a cost effective single use reamer with a novel blade and assembly design that improves cutting efficiency. The enhanced reaming efficiencies of the present invention decrease procedural times and minimize patient trauma. The hemispherical reamer of the present invention ensures sharpness and cleanliness that promotes optimal patient outcomes.

SUMMARY OF THE INVENTION

The present invention provides a disposable reamer for shaping either concave or convex surfaces. The reamer of the present invention comprises a reamer body and a plurality of blades that are incorporated along a curved surface of the body.

The reamer body of the present invention is generally of a semi-hemispherical form, similar to that of a cup or a shell. Accordingly, the reamer body comprises a concave interior portion and a convex outer portion. In one embodiment, the plurality of reamer blades is incorporated along the curved interior surface within the concave portion of the body. In a preferred embodiment, the blades are aligned along the curved concave surface of the body such that the respective cutting edges face away toward the interior region of the shell in the direction of rotation.

In a second embodiment, the plurality of reamer blades is aligned with the curved outer surface of the convex portion of the reamer body shell. In this embodiment, the blades are positioned along the outer convex surface of the reamer body such that the blade cutting edges are facing outwards and in the direction of rotation.

In a featured embodiment of the present invention, the reamer blades are comprised of a series of discrete cutting teeth that are aligned in a linear row. The linear row of blades is further positioned along the curved surface of the body shell of the reamer. The series of discrete cutting teeth may be positioned along the curved concave interior surface of the body shell or alternatively, may be positioned along the curved convex outer surface of the shell. In either case, the reamer blades are preferably composed of a metallic material such as stainless steel, MP35N, titanium, and the like.

In a preferred embodiment, the reamer of the present invention comprises four linear rows of blades. Each of the rows is positioned such that they reside along the curved surface of the concave or convex portions of the sidewall of the reamer shell. Each of the four rows of blades lies within a quadrant of the concave or convex portion of the body. Specifically, each of the four linear rows of blades is positioned parallel to one of two imaginary planes perpendicular to each other that bisect the shell of the reamer. Furthermore, each of the rows of blades is aligned such that they are offset a distance from the imaginary bisecting plane. The offset position and parallel orientation with respect to the bisecting plane produces a reamer capable of efficient bone cutting action.

Each of the reamer blades has a cutting portion that fluidly extends from a planar portion. A gap separates each of the cutting surfaces that comprise the cutting portion of the reamer blade thus creating a series of discreet cutting teeth. The planar portion of the blade is designed to mate along the curved concave surface of the body or is positioned such that it resides along the contour of the curved convex surface of the body. Alternatively, the linear series of blades may be bonded within a slot that is formed within the curved sidewall surface of the body. The opposing, cutting edge portion of a blade is bent at an angle away from the planar surface of the blade. The cutting edge is further angled from the planar surface of the blade in the direction of rotation of the reamer. It is the series of angled discrete cutting edges in combination with the offset distance that increases the cutting efficiency of the reamer of the present invention.

The reamer body is designed with a perpendicular axis that is coincident with the axis of rotation of the device. This feature enables the reamer body and accompanying reamer blades to rotate in a controlled manner about the bone or tissue that is to be cut. The reamer body is preferably composed of a polymeric material, such as polyetherether ketone (PEEK) or acrylonitrile butadiene styrene (ABS). The reamer body may also comprise a series of openings that extend through the wall of the frame. These openings are designed to facilitate removal of bone and tissue.

During the manufacturing process, each linear row of blades is aligned along the curved concave surface of the reamer body either in direct contact with the curved surface of the sidewall of the body or residing within respective blade slots. Once positioned along the curved surface of the reamer frame, the blades are bonded thereto via an induction heating process. During this induction heating process, the reamer assembly is subjected to a heat source that melts the surrounding material of the reamer frame. The melted material flows covering the surface of the blade attachment portion. The flowing molten material then penetrates through the blade engagement openings, creating a fluid connection between the frame and the insert reamer blade, thereby bonding each blade to the frame. This low cost production process avoids the need for expensive grinding operations and can use simple stamping or chemical etching to form the reamer blades. Alternatively, an adhesive material may be used to bond the reamer blades to the surface of the reamer body.

In addition, a reamer connector shaft may also be provided. The reamer shaft can be removably attached to the interface portion of the reamer. Alternatively, the shaft may be provided with an interference fit, a locking junction, or can be designed as an integral portion of the reamer. In either case, the opposite end of the shaft is designed to connect to a motor to provide rotational torque to the reamer.

DETAILED DESCRIPTION OF THE INVENTION

Figure 1:
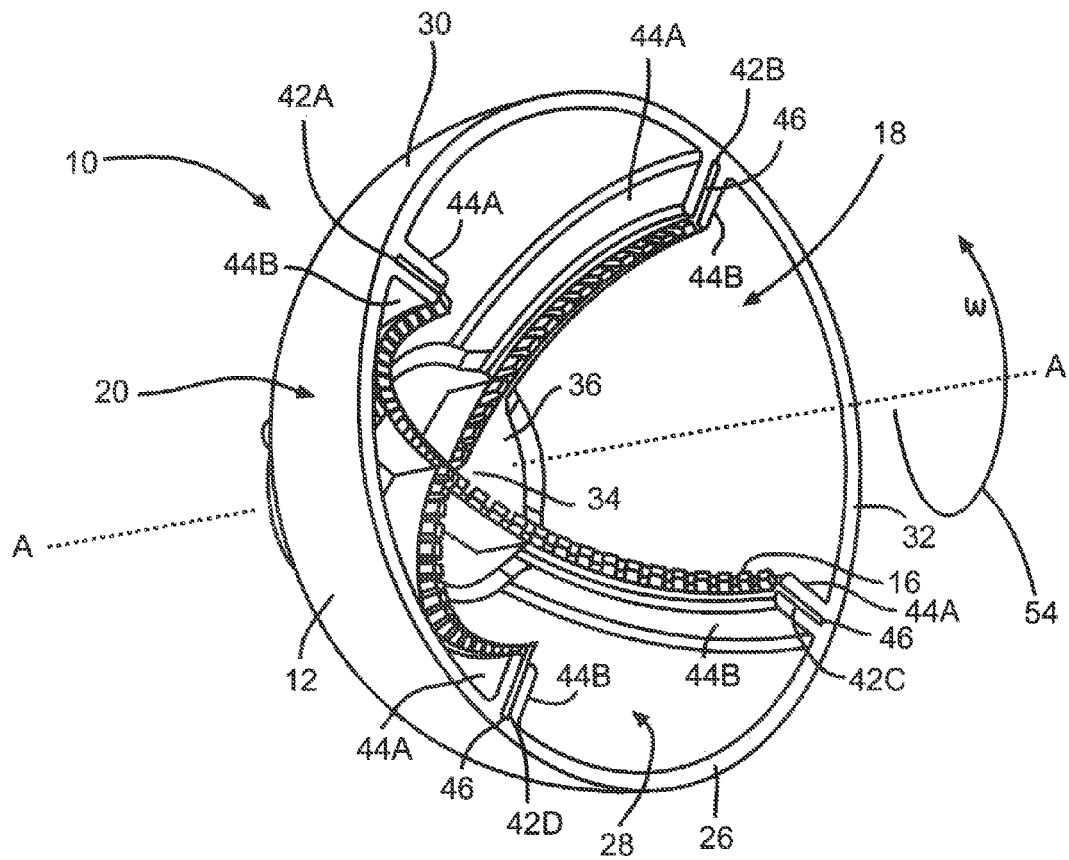
FIG. 1 illustrates a perspective view of an embodiment of the reamer of the present invention.
Figure 2:
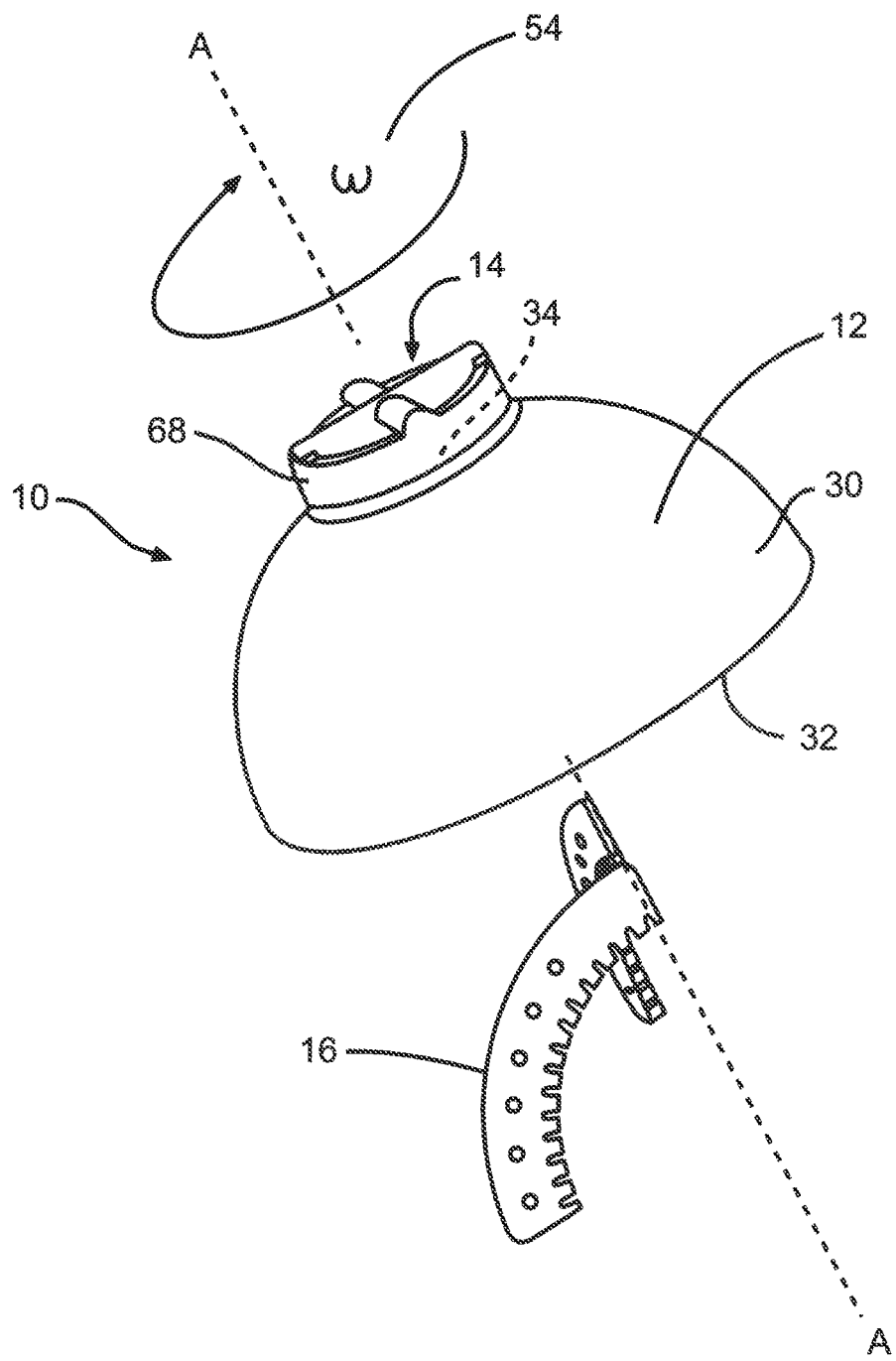
FIG. 2 illustrates a perspective view of an embodiment of the reamer body and reamer blades shown in FIG. 1.
Figure 5:
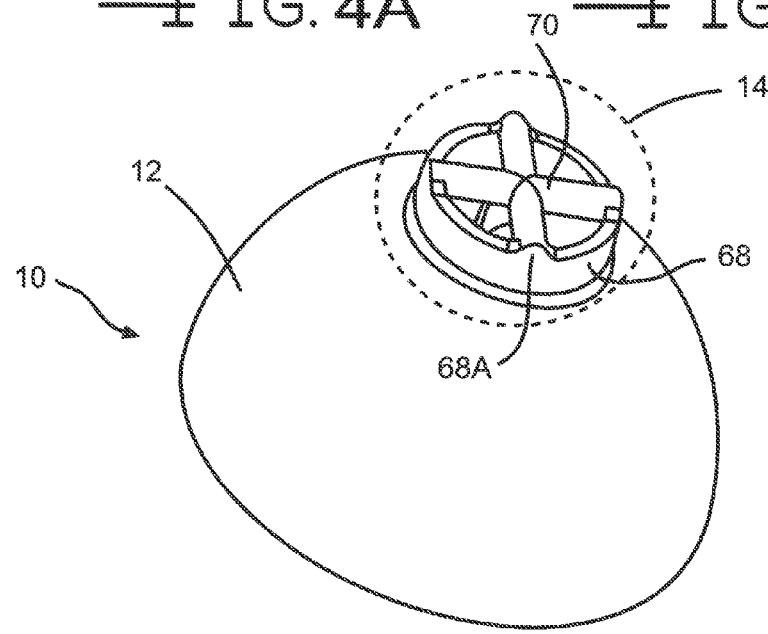
FIG. 5 shows a perspective view of reamer body and attachment portion.

Now turning to the figures, FIGS. 1-2 and 5 illustrate an embodiment of an orthopedic reamer 10 of the present invention. As shown, reamer 10 comprises a reamer body portion 12, a shaft engagement portion 14 (FIG. 2) and a series of reamer blades 16 that are incorporated with the body portion 12. The reamer body 12 of the present invention is generally of a semi-hemispherical form, similar to that of a cup or shell. Accordingly, the body 12 comprises a curved interior sidewall surface 18 and a curved outer sidewall surface 20. In a first embodiment of the reamer 10 of the present invention, the reamer blade 16 of a concave embodiment is positioned lengthwise along the curved interior sidewall surface 18 of the body 12. In a second embodiment of the reamer 22 (FIG. 9) of the present invention, a reamer blade 24 of a convex embodiment is positioned lengthwise along the curved outer surface of the body.

Figure 3:
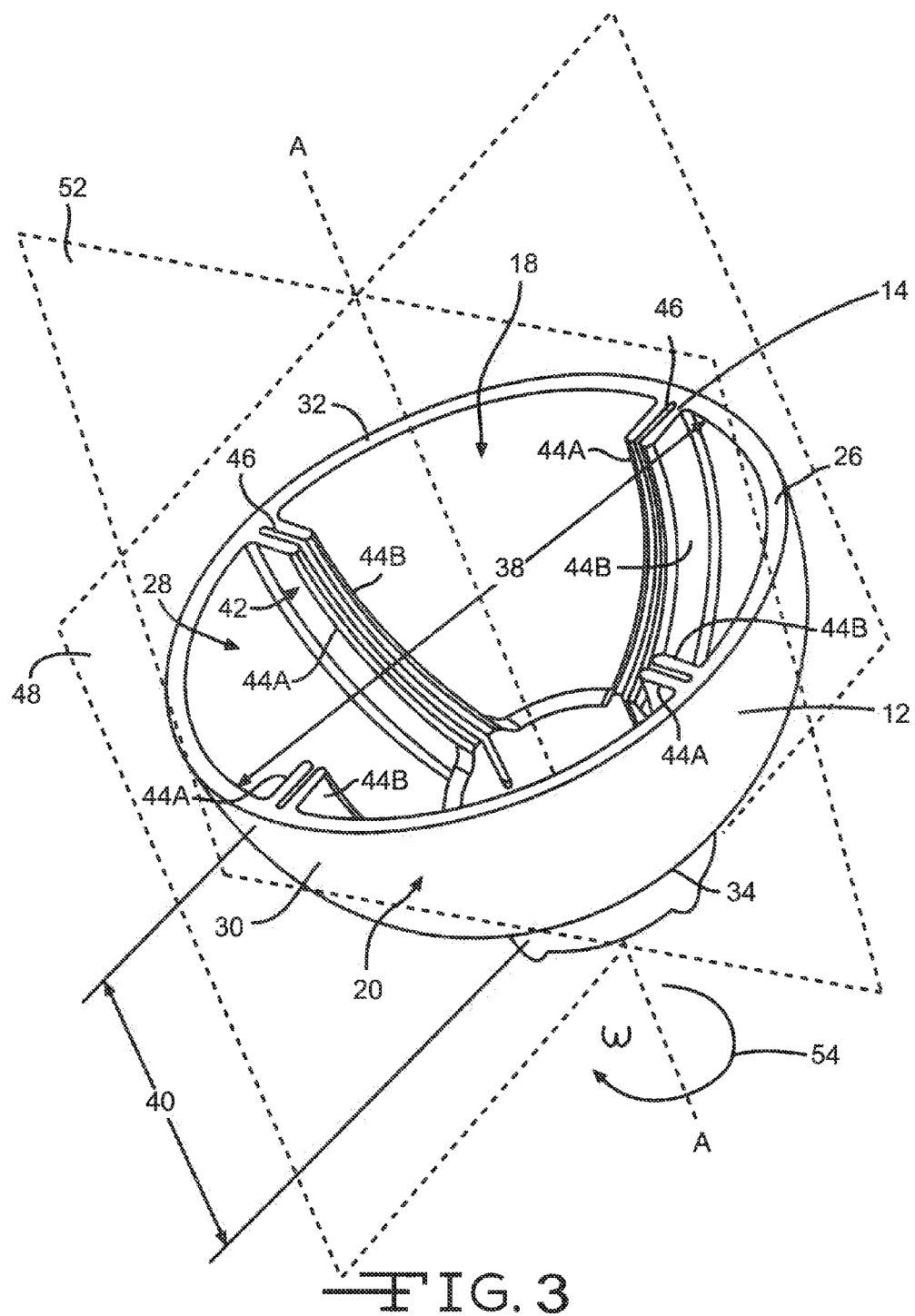
FIG. 3 shows a perspective view of an embodiment of a reamer body.

With regards to the first embodiment of the reamer 10 of the present invention, the reamer body portion 12 preferably comprises a curved sidewall 26 that encompasses an interior region 28. As shown in FIGS. 1 and 3, the sidewall 26 has a curved interior surface 18. More specifically, the body portion 12 is of a generally semi-hemispherical shell form such that the interior sidewall surface 18 of the sidewall 26 is concave. The reamer body 12 further comprises a body base portion 30 with a lower edge 32. Preferably the shell is half of a hemisphere with the lower edge 32 residing along an imaginary equatorial plane. In a preferred embodiment, the hemispherical shell curves upwards from the lower edge 32 of the base portion 30 to an apex 34 that is located about the center of the hemispherical shell. An opening 36 is positioned through the sidewall 26 at the apex 34. As shown, a perpendicular axis A-A extends through the apex opening 36 of the shell body 12. Axis A-A defines a rotational axis of the reamer 10 during use.

In a preferred embodiment, the base portion 30 has a diameter 38 ranging from about 1 cm to about 10 cm and a body height 40 ranging from about 1 cm to about 10 cm. The sidewall 26 of the body 12 has a thickness ranging from about 1 mm to about 5 mm. The reamer body 12 is designed such that the diameter of the base 30 is greater than the opening 36 at the apex 34. Furthermore, the body portion 12 is preferably composed of a polymeric material, such as acroylonitrile butadiene styrene (ABS), polyarylamide, polyetheretherketone (PEEK), or the like.

As shown in FIGS. 1 and 3, a series of slots 42 may be positioned along the curved interior surface of the body shell 12. As shown, each slot 42 has opposing slot sidewalls 44A, 44B, that extend along the interior surface 18 of the sidewall 26. A slot groove 46 resides between the opposing sidewalls 44A, 44B. Each slot 42 is preferably designed such that a concave reamer blade 16 is positioned therewithin. In a preferred embodiment, there are four slots 42A, 42B, 42C, 42D, (FIG. 1) each of the slots having opposing slot sidewalls 44A, 44B, that extend lengthwise from the apex 34 to the lower edge 32 of the base 30 of the body 12. Thus, each of the concave reamer blades 16 preferably extends lengthwise from the apex to the lower edge 32 of the base 30. Alternatively, the slots 42 may be designed such that they reside within a portion of the thickness of the interior sidewall surface 18.

Figures 4A, 4B:
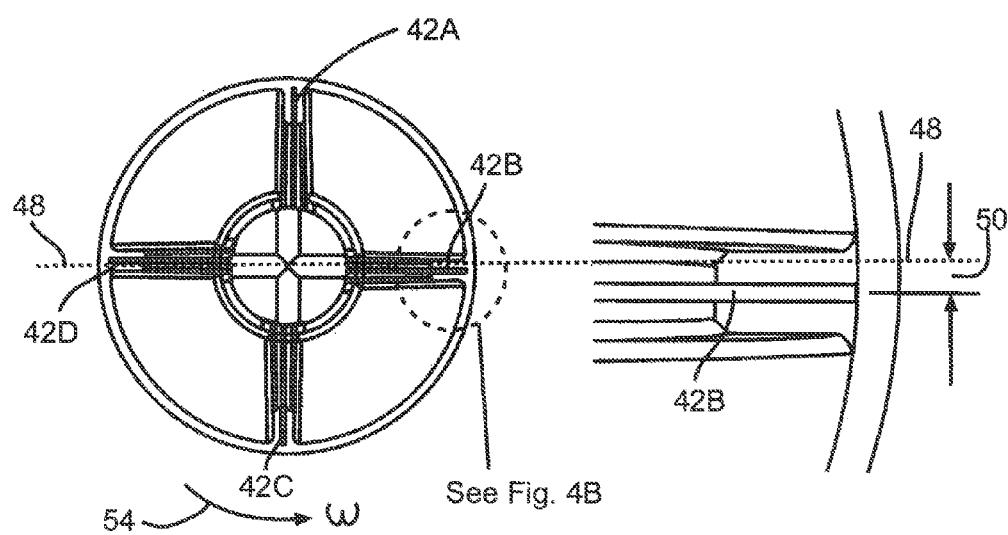
FIGS. 4A and 4B illustrate an embodiment of the offset of the reamer blade within the reamer body.

As shown in FIGS. 1, 3, 4A, and 4B, the slots 42 are preferably positioned along the curved interior surface of the body 12 such that they extend lengthwise about parallel to an imaginary plane 48 that bisects the body shell 12. In addition, the slots 42 are positioned such that there is an offset distance 50 separating the lengthwise oriented slot 42 from its respective bisecting plane 48 (FIG. 4B). More specifically, each slot 42 is positioned along the curved interior surface 18 of the sidewall 26 of the body 12 such that the length of the slot 42 lies about parallel to, and is offset a distance from, the imaginary plane 48 that bisects the hemispherical shell. As shown in FIG. 3, there are two imaginary bisecting planes 48, 52. The bisecting planes 48, 52 are perpendicular to each other and intersect along the perpendicular axis A-A. A bisecting plane is herein defined as an imaginary plane that extends through the semi-hemispherical shell dividing the shell into two equal parts. For example, slot 42A is positioned lengthwise parallel to imaginary plane 52, and slot 42D is positioned lengthwise parallel to imaginary plane 48.

The offset is defined herein as the distance measured from the center or midline of the slot groove 46 to the imaginary bisecting plane 48, 52 that extends about parallel to the slot 42. Thus, when the reamer blade 16 is positioned within the slot, the offset distance is measured from the centerline of the length of the blade to the bisecting plane 48, 52 that extends about parallel to the length of the blade 16. In a preferred embodiment, the length of the offset distance 50 ranges from about 0.5 mm to about 5 mm. The offset design of the reamer blades 16 enables the reamer 10 to cut in an efficient hemispherical path once it begins rotation about its rotational axis 54.

FIGS. 2, 6, 7 and 13 illustrate embodiments of the concave and convex reamer blades 16, 24 of the present invention. In a preferred embodiment, the blades are composed of a biocompatible material such as stainless steel, 316-stainless steel, titanium, MP35N, or combinations thereof.

Figure 6:
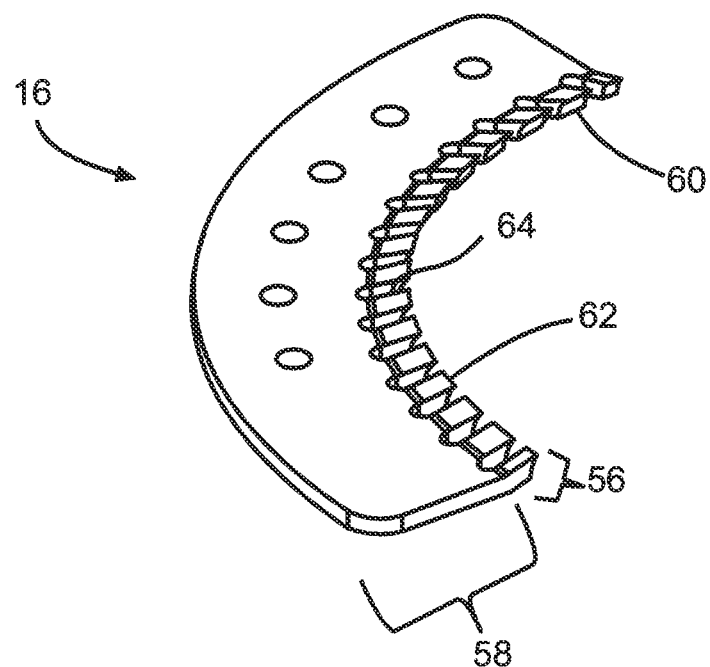
FIG. 6 illustrates a perspective view of an embodiment of a reamer blade.
Figure 7:
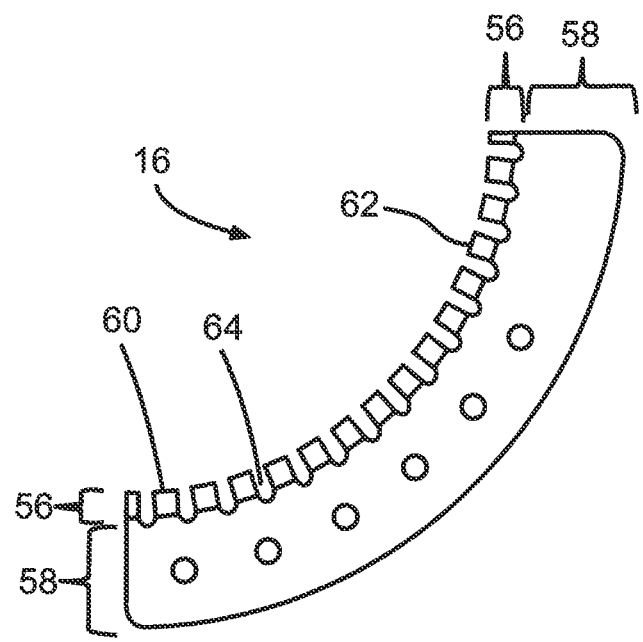
FIG. 7 shows a side view of the reamer blade shown in FIG. 6.
Figure 13:
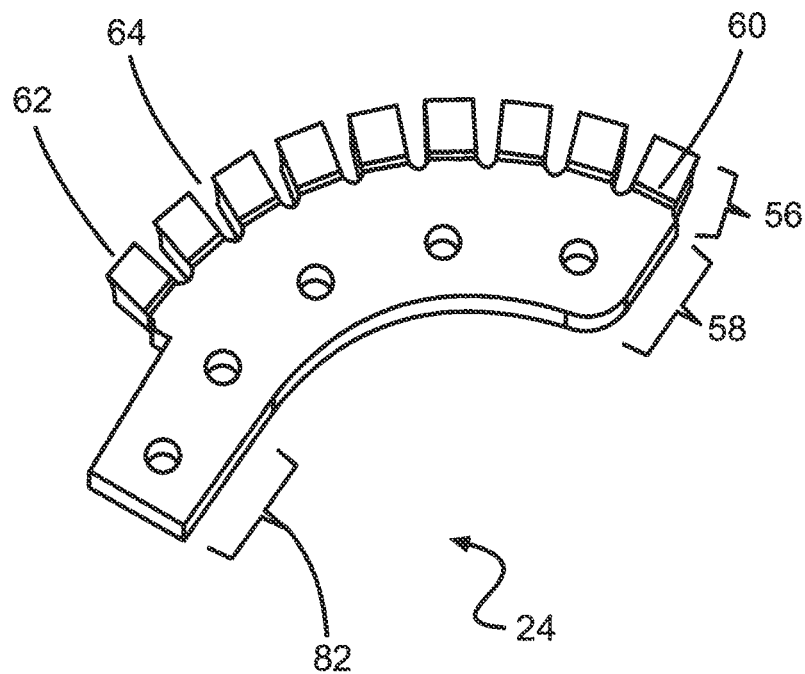
FIG. 13 shows a magnified perspective view of an embodiment of a reamer blade shown in FIG. 10.

As shown, the blade 16 comprises a cutting portion 56 that fluidly extends from a planar blade portion 58. The cutting portion 56 is positioned along the curved, concave side of the blade 16. It should be noted that both concave and convex embodiment blades 16, 24 comprise a cutting portion 56 that extends from a planar portion 58. The difference between the concave and convex blades 16, 24 resides in the position of the cutting portion 56 along the curvature of the blade. The cutting portion 56 for concave blade 16 lies along the concave blade bend whereas the cutting portion 56 for convex blade 24 lies along the convex blade bend as shown in FIGS. 6, 7 and 13. In the case of concave blade 16, the planar portion 58 is preferably positioned within the groove 46 of the slot 42 of the reamer body 17. As illustrated in FIG. 1, the curved convex side edge of the planar portion 58 of blade 16 is positioned within the groove 46 of the slot 42.

Figure 1A:
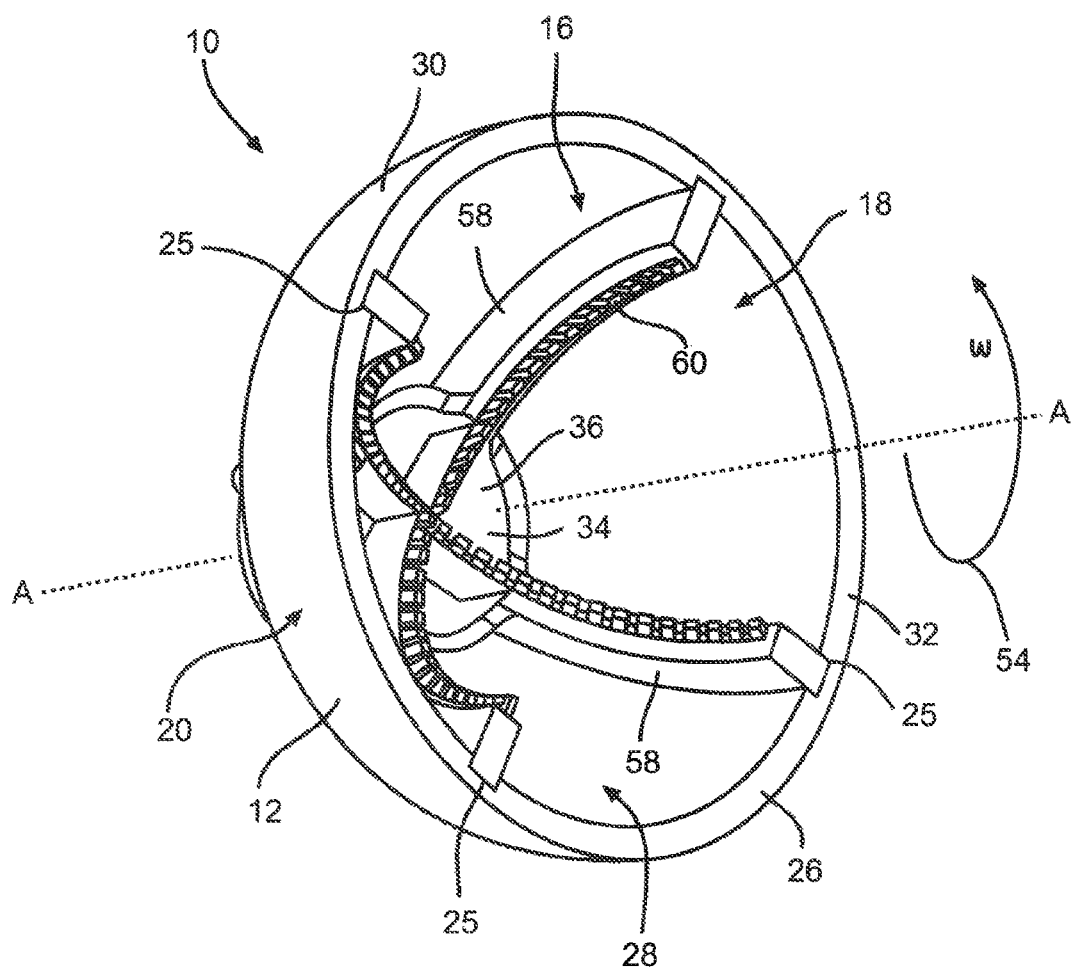
FIG. 1A shows a perspective view of an alternative embodiment of the reamer shown in FIG. 1.

Alternatively, blade 16 may be positioned directly along the interior surface of the body shell 12. In this alternative embodiment (not shown), the convex side edge surface of the planar portion 58 of the blade is directly adhered to the interior concave shell surface 18 of the body 12. As shown in FIG. 1A, the convex side edge surface of the planar portion 58 of blade 16 resides within a recessed groove or slot 25 partially extending within the interior surface 18 of the body 12. In these embodiments, the blade 16 is positioned lengthwise such that it is parallel to, and offset from, bisecting plane 48, 52, similar to the position of the blade slot 42 as previously discussed.

In a preferred embodiment, the cutting portion 56 comprises a series of discrete cutting teeth 50, each of them comprising a cutting edge 62. In a preferred embodiment, the cutting teeth 60 are separated from each other by a gap 64. As shown in FIGS. 6-7 and 13, each of the gaps 64 extends through the cutting portion and partially into the planar portion 58 thereby creating discrete reamer teeth 60. These gaps 64 are strategically positioned between each tooth of the blade 16, 24. That's to minimize contact of the cutting edge 62 with the surface being cut, thereby reducing the force required to cut the surface.

Figure 8:
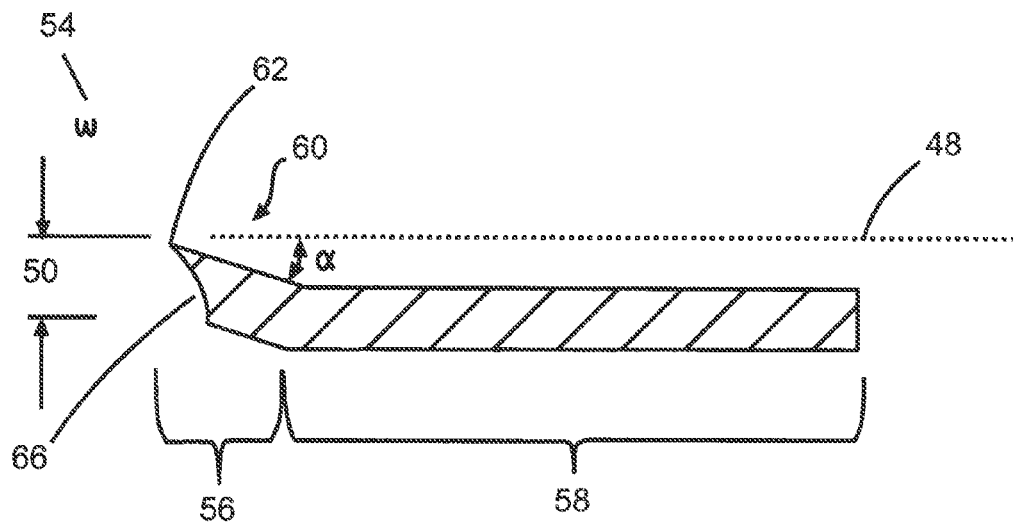
FIG. 8 illustrates a magnified cross-section view of an embodiment of a reamer tooth.

FIG. 8 shows a detailed view of the section profile of the concave blade 16. The leading surface of the cutting edge 62 and the bisecting plane 48, 58 define a rake angle α at the point where the hemispherical surface to be cut. In a preferred embodiment, the rake angle α may range from about 0° to about 30°. A positive rake angle α is beneficial in that it encourages a more direct cutting motion of the blade and avoids a scraping method of cutting. It is, therefore, apparent that by bending the cutting teeth 60 and offsetting the blade from its bisecting plane, a non-zero, positive rake angle can be created. In a preferred embodiment, the leading edge of the blade cutting edge 62 lies within the bisecting plane 48, 52. This embodiment helps ensure that a complete 180 hemispherical cut is achieved. Furthermore, both concave and convex reamer blade embodiments 16, 24 comprise a cutting edge as embodied in FIG. 8. Regardless of the orientation of the cutting teeth 60 of the present invention, whether the blade is a concave style blade or a convex style blade, the design and orientation of the cutting teeth 60, illustrated in FIG. 8, applies to both blade embodiments.

In a preferred embodiment, the cutting edge 62 of each of the teeth 60 is angled in a direction facing the desired direction of rotation. In addition, the rake angle α allows the cutting edge 62 of the blade to remove both hard and soft bone and tissue using a skiving or cutting method. The cutting edge 62 is thus curved to precisely follow the contour of the intended surface being cut. As shown in FIG. 8, a relief surface 66 is provided at the trailing surface behind the cutting edge 62. That's so as to not interfere in any way with the surface being cut. Moreover, the cutting teeth 62 from one blade to the next are staggered so that a gap between adjacent teeth of one blade is cut by a tooth 62 of a following blade. That way, a smooth cut surface is formed, such as a smooth semi-hemispherical cut surface without ridges or a rough contour.

As shown in FIG. 5, an embodiment of the shaft engagement portion 14 is positioned on the convex side of the reamer body 12. As shown in the illustrated embodiment, the shaft engagement portion 14 comprises a shaft engagement annular sidewall 68 that is raised from the surface of the body 12. The sidewall 68 is centered over the apex opening 36 of the body 12. A cross bar 70 is positioned within the opening of the annular sidewall 68. The ends of the bars forming the cross 70 are directly connected to an inner surface of the sidewall 68. Preferably, the sidewall 68 has lobes 68A where the cross bar ends connect. The engagement portion 14 is constructed such that a reamer shaft (not shown) may be releasably connected to the cross bar 70. A motor (not shown) may then be attached to the shaft to provide rotation to the reamer.

FIGS. 9-12 illustrate the second alternate embodiment of the reamer 22 of the present invention. Similar to the first reamer 10 shown in FIGS. 1 and 2, reamer 22 comprises a body portion 72, a series of reamer blades 24 and a shaft attachment portion 74. Also, similar to the reamer body 12 of the first embodiment, the reamer body illustrated in FIGS. 9-11 of the present invention, is generally of a semi-hemispherical form, like that of a cup or shell. Preferably the shell is half of a hemisphere with the lower edge 81 residing along an imaginary equatorial plane. The reamer body 72, shown in FIG. 11, comprises a curved inner surface 76 and a curved outer surface 78. More specifically, the reamer body 72 of reamer 22 comprises a concave interior region and a convex outer surface 78. However, unlike the reamer 10 of the first embodiment, as previously discussed, convex reamer blades 24 are positioned within the body 72. More specifically, the convex blades 24 are positioned such that the cutting portion 56 of the blade 24 protrudes though a series of corresponding slits 80. These series of slits 80 extend through the thickness of the curved exterior sidewall of the body 72.

Figure 9:
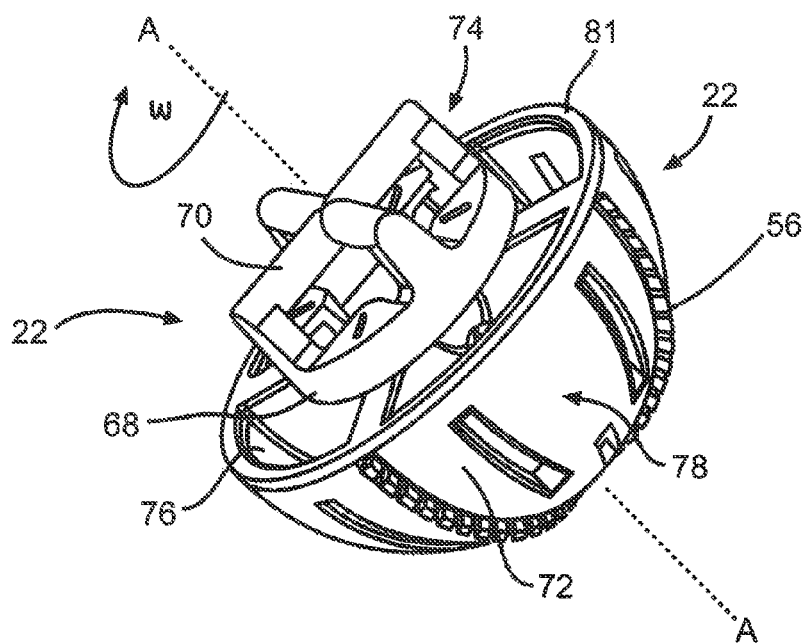
FIG. 9 illustrates an alternative embodiment of the reamer of the present invention.
Figure 10:
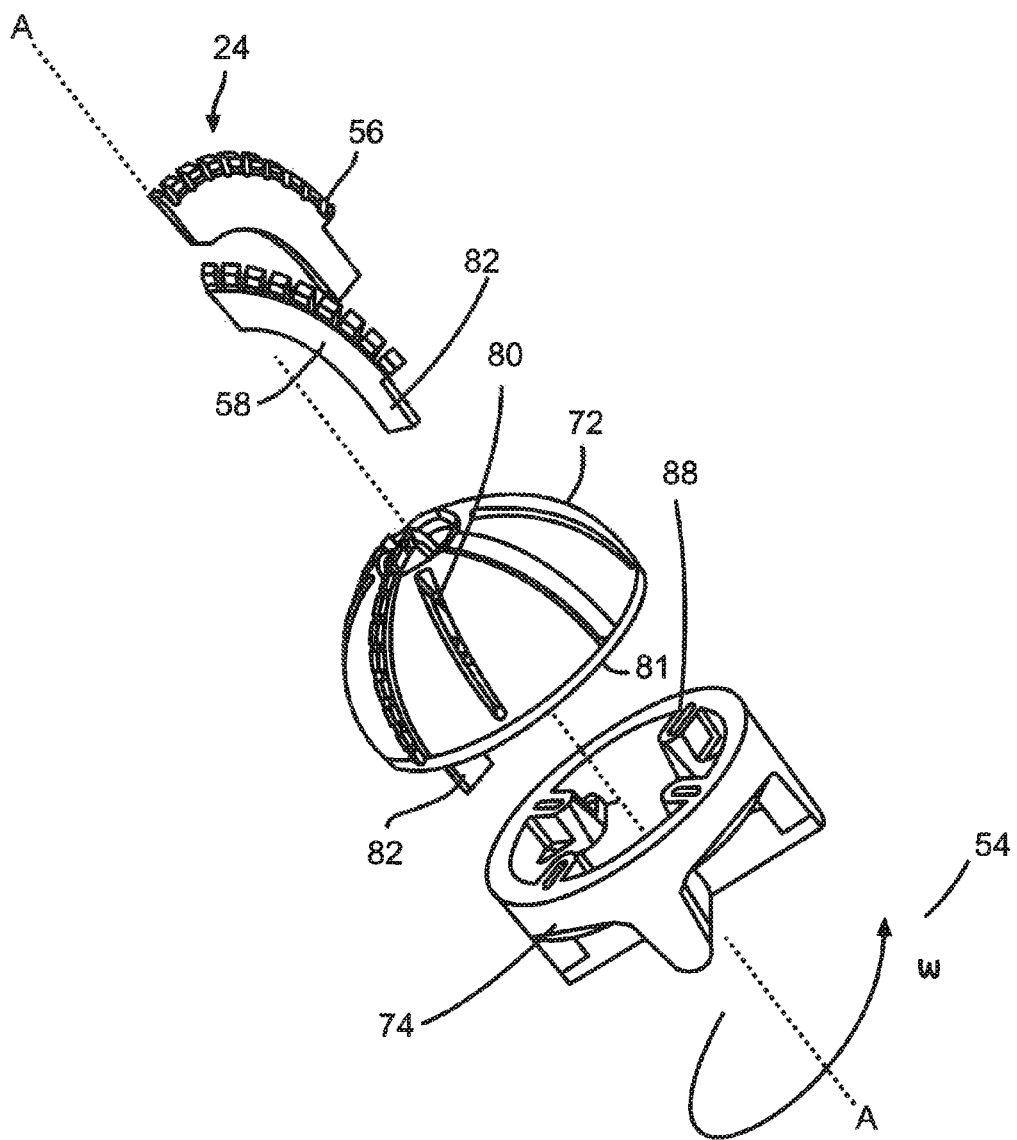
FIG. 10 shows a perspective view of the components comprising the reamer shown in FIG. 9.
Figure 11:
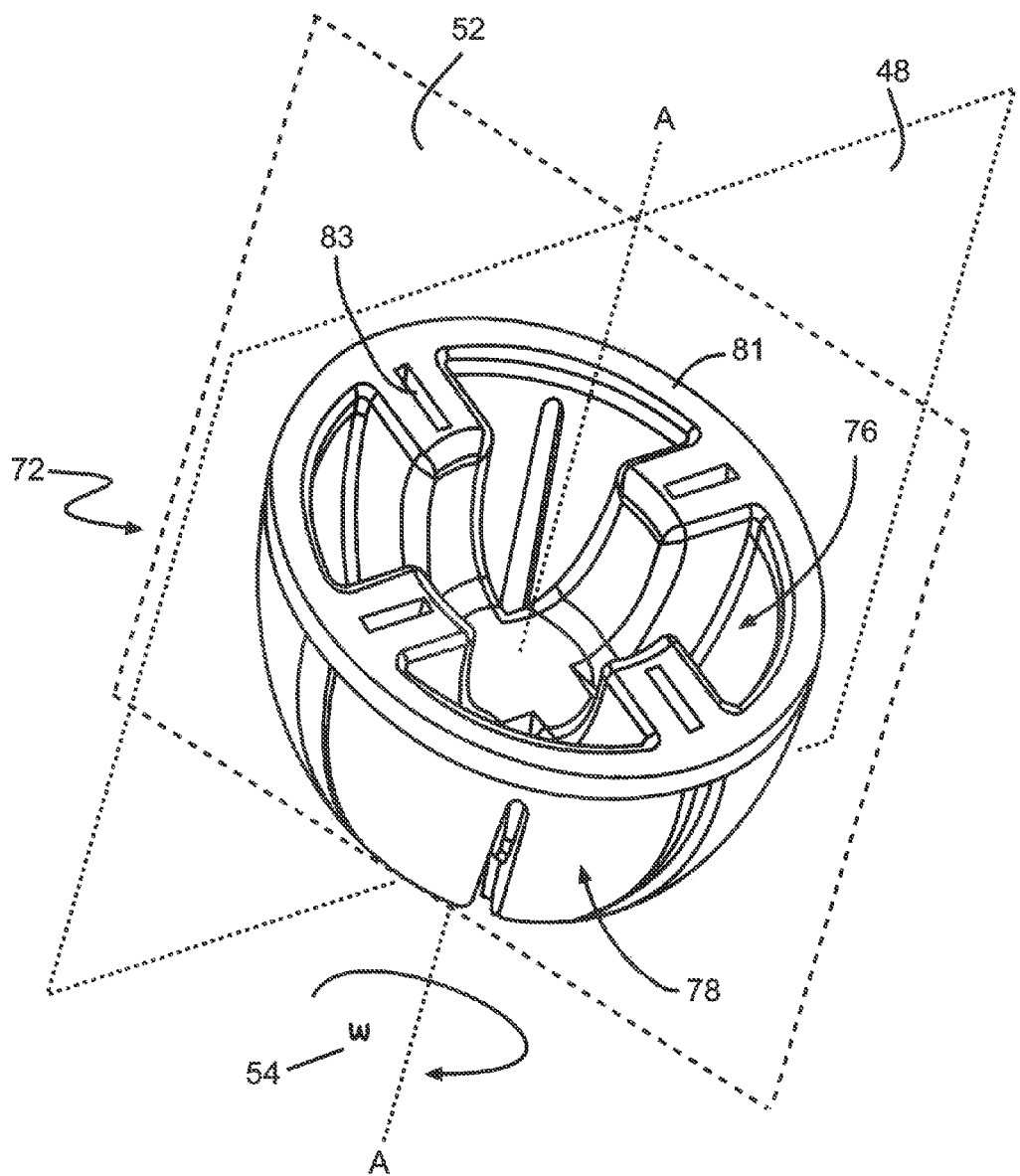
FIG. 11 illustrates a perspective view of an alternative embodiment of a reamer body.
Figure 12:
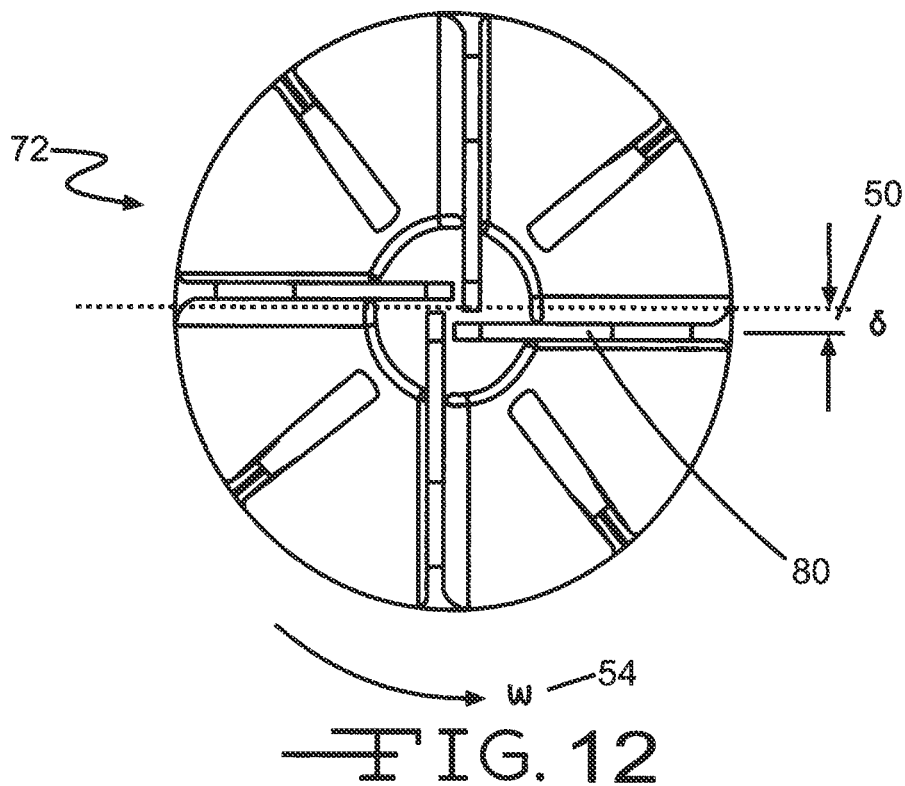
FIG. 12 shows a top view of the reamer body shown in FIG. 11.

As illustrated in FIGS. 9 and 10, the reamer 22 is designed with the series of cutting teeth 60 extending through their respective slit opening 80. Similar to the blade slots 42 of reamer 10, as previously described, the blade slit openings 80 are positioned parallel and offset from a corresponding bisecting plane. Like the reamer of the first embodiment, the orientation of the slit openings 80 positions the cutting portion 56 of the convex reamer blade 24 to enable a cut in an efficient hemispherical path about its rotational axis 54.

As shown in FIGS. 10 and 13, the convex reamer blades 24 are constructed such that the cutting portion 56 and cutting teeth 60 are positioned about the outward curvature of the blade 24. The outward curvature defined by a reamer blade radius is of curvature that ranges from about 1 cm to about 10 cm. In a preferred embodiment, the convex blades 24 are composed of a biocompatible material such as stainless steel, more preferably, 316-stainless steel. Other biocompatible metals such as titanium, MP35N, and combinations thereof may also be used.

Similar to the concave reamer blade 16 of the previous embodiment, the convex reamer blade 24 comprises a planar blade portion 58 spaced from a cutting portion 56. A tab 82 portion extends from the end of the planar portion as shown in FIG. 13. When correctly positioned within the reamer body 72, the cutting portion 56 is positioned within the slit 80 of the reamer body 72. The planar portion 58 is preferably anchored within the reamer body 72 with the tab portion 82 extending past the base of the reamer body 72 extending through opening 83.

Similar to the concave reamer blade 16, the cutting portion 56 of the convex reamer blade 24 comprises a series of discrete cutting teeth 60, each of the cutting teeth 60 are separated from each other by a gap 64. These gaps 64 are strategically positioned between each tooth of the blade 60 to minimize contact of the cutting edge 62 with the surface being cut, thereby reducing the forces required to cut the surface. In addition, each of the teeth 60 of the convex blade 24 comprises a cutting edge 62 has an associated rake angle and is positioned a skew from the planar portion 58 of the blade 24. The cutting portion 56 is also angled in a direction towards the desired direction of rotation. Moreover, the cutting teeth 62 from one blade to the next are staggered so that a gap between adjacent teeth of one blade is cut by a tooth 62 of a following blade. That way, a smooth cut surface is formed, such as a smooth semi-hemispherical cut surface without ridges or a rough contour.

Figure 14:
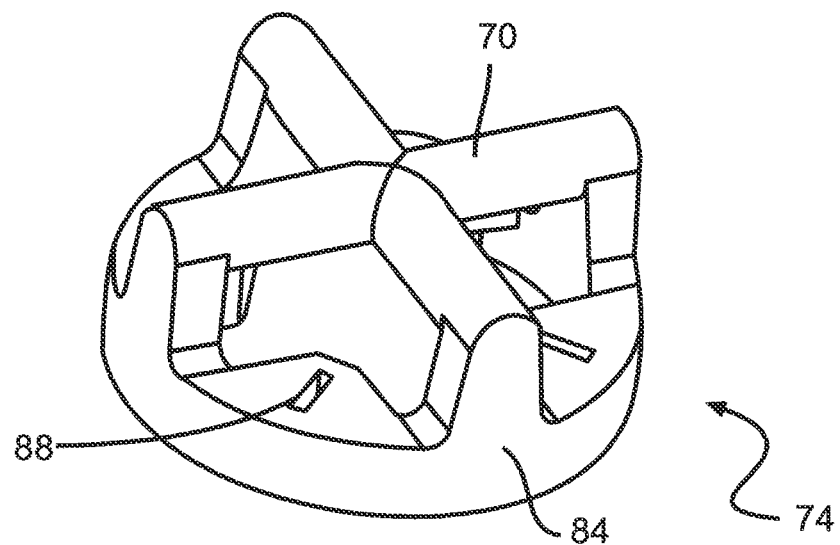
FIGS. 14 and 15 illustrate different embodiments of a shaft engagement portion.
Figure 15:
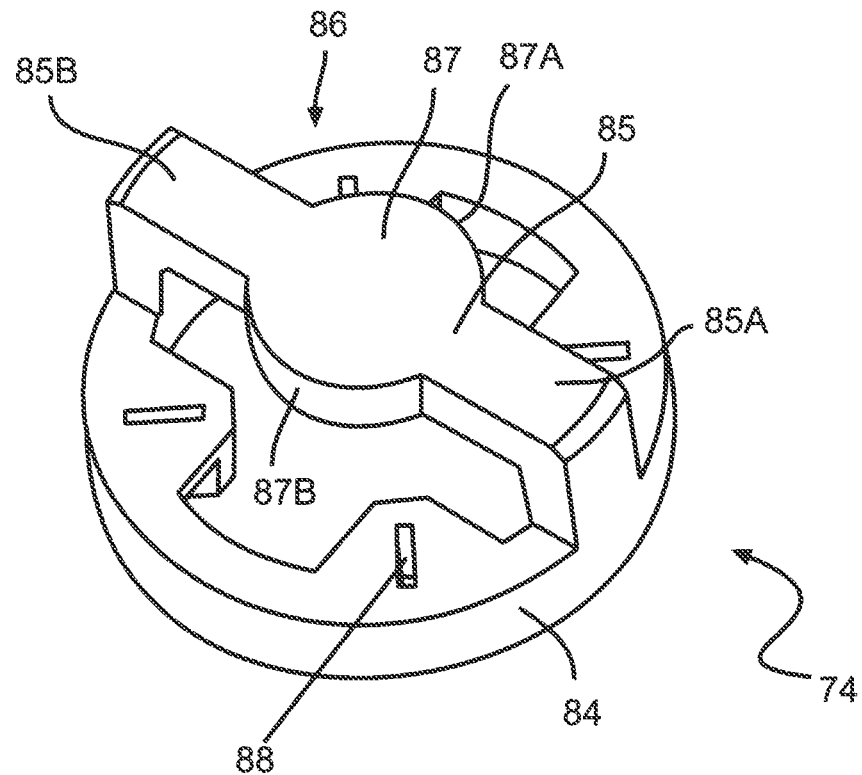

As illustrated in FIGS. 9, 10, 14-15, connected to the base portion of the reamer body 72, is positioned a convex reamer adapter 74. The adapter 74 comprises an annular adapter sidewall 84 with perpendicular cross bars positioned therewithin. Alternatively, as shown in FIG. 15, the convex adapter 74 may comprise a boss plate 86 instead of the cross bars 70 as illustrated in FIG. 14. The boss plate 86 comprises a retaining bar 85 with spaced apart first and second retaining bar sides 85A, 85B extending to the base periphery and located on opposite sides of the longitudinal axis of the retaining bar 85 and a central retaining bar structure 87 substantially centered between where the opposed ends of the retaining bar attach to the base periphery, the central retaining bar structure having opposed first and second radiused sides 87A, 87B extending beyond respective planes of the first and second retaining bar sides, the opposed first and second radiused sides being aligned with each other along a perpendicular axis bisecting the longitudinal axis of the retaining bar. A more detailed description of the boss plate embodiment adapter is given in U.S. Pat. No. 7,588,572, to White et al., which is assigned to the assignee of the present invention and incorporated herein by reference. In either embodiment, the adapter 74 has a series of adapter slots 88 within which the convex blade tabs 82 reside therewithin.

As shown in Table 1 below, the embodiments of the reamer 10, 22 of the present invention were tested against reamers that are commercially available from Acumed® USA of Hillsboro, Oreg. As shown below, an Acumed® 24 mm cup and cone style reamer were tested against the respective first and second embodiments of the reamer 10, 22 of the present invention. In the comparison, all reamers were set to a rotation speed of about 1,600 RPM and were used to cut samples of a urethane test material to simulate the cutting of bone. As the reamers cut the test material, their respective torque values were recorded.

| Reamer | Trial 1 | Trial 2 | Trial 3 | Average |
|---|---|---|---|---|
| Acumed ® Cup | 3.4 Nm | 2.5 Nm | 2.7 Nm | 2.87 Nm |
| Acumed ® Cone | 3.2 Nm | 3.0 Nm | 2.9 Nm | 3.03 Nm |
| Embodiment 1 | 1.4 Nm | 0.8 Nm | 1.2 Nm | 1.13 Nm |
| Embodiment 2 | 2.3 Nm | 2.0 Nm | 1.7 Nm | 2.00 Nm |

As shown in the results table above, the average measured torque value for the reamer of embodiment 1 was 1.13 Nm. In comparison, the measured average torque value for the Acumed® Cup style reamer was 2.87 Nm. Per the test results above, the reamer 10 of the first embodiment of the present invention achieved an average lower measured torque value of 1.74 Nm in comparison to the Acumed® cup style reamer. This is an improvement of about 61 percent of increased torque efficiency as compared to the Acumed® model. Likewise, the reamer 22 of the second embodiment of the present invention achieved a measured torque value of 2.00 Nm. In comparison, the Acumed® cone style reamer achieved an average measured torque value of 3.03 Nm. Thus, an improvement of about 1.03 Nm, equally about a 34 percent increase in torque efficiency was achieved in comparison to the Acumed® Cone style reamer.

Thus the design features of the reamer 10, 22 of the present invention enables efficient removal of both hard and soft bone and tissue using a skiving or cutting method. The cutting edge 62 is thus curved to precisely follow the contour of the surface being cut. The offset blade design, in combination with the use of the cutting teeth rake angle, provides a reamer capable of more efficient hemispherical cutting of both tissue and bone.

Accordingly, the invention is not limited, except by the appended claims.

What is claimed is:
1. A reamer, comprising:
 a) a shell, comprising:
  i) a shell sidewall having a convex exterior surface spaced from an interior surface by a shell thickness, wherein the shell extends from an apex to a lower shell edge, the shell being detachably connectable to a reamer shaft for rotational movement about a rotational axis that extends through the apex and is aligned perpendicular to an imaginary edge plane at the lower shell edge, and wherein a first imaginary bisecting plane and a second imaginary bisecting plane intersect the rotational axis and the imaginary edge plane offset 90° from each other;
  ii) a first slit through the shell thickness, the first slit extending from at or adjacent to the lower shell edge and toward the first imaginary bisecting plane, wherein the first slit is spaced clockwise from the second imaginary bisecting plane with respect to a view looking along the rotational axis toward the lower shell edge; and
  iii) a second slit through the shell thickness, the second slit extending from at or adjacent to the lower shell edge and toward the first imaginary bisecting plane, wherein the second slit is spaced clockwise from the second imaginary bisecting plane with respect to the rotational axis, but on an opposite side thereof with respect to the first slit; and
 b) a first reamer blade and a second reamer blade, each blade comprising a blade sidewall extending from a proximal blade portion to a distal cutting portion, the first and second blades received in the respective first and second slits with their respective distal cutting portions comprising a plurality of first and second cutting teeth extending outwardly from the exterior shell surface.

2. The reamer of claim 1 wherein with the first and second blades received in the respective first and second slits, each blade comprises an imaginary blade plane aligned along the sidewall of the proximal blade portion and extending through the distal cutting portion and wherein each of the plurality of cutting teeth of the first and second blades has a cutting edge that lies along an imaginary cutting plane, and wherein a rake angle extends along a cutting tooth between the imaginary blade and cutting planes with respect to the imaginary edge plane of the shell.

3. The reamer of claim 1 wherein each of the plurality of cutting teeth comprises a relief surface provided at a trailing surface of the distal cutting portion, the trailing surface residing between opposed first and second surfaces of the blade sidewall comprising the proximal blade portion.

4. The reamer of claim 1 wherein the shell is a portion of a hemisphere and the imaginary edge plane resides at an imaginary equator of the hemisphere.

5. The reamer of claim 1 wherein the first and second slits are formed from opposed slit sidewalls that extend from the shell interior surface toward the rotational axis.

6. The reamer of claim 5 wherein the blade proximal portion for each of the first and second reamer blades is removably positionable between the opposed slit sidewalls comprising the respective first and second slits.

7. The reamer of claim 1 wherein the reamer blade is composed of a metallic material selected from the group consisting of stainless steel, MP35N, titanium, and combinations thereof.

8. The reamer of claim 1 wherein the reamer body is composed of a biocompatible polymeric material selected from the group consisting of acroylonitrile butadiene styrene (ABS), polyarylamide, polyetheretherketone (PEEK), and combinations thereof.

9. The reamer of claim 1 wherein a first opening extends through the shell thickness to provide a passageway for tissue to pass therethrough.

10. The reamer of claim 1 wherein a shaft engagement portion configured for detachable connection to a source of rotary drive motion is connected to the shell at or adjacent to the lower shell edge.

11. The reamer of claim 10 wherein the shaft engagement portion comprises a retaining bar with spaced apart first and second retaining bar sides extending to a base, and wherein a central retaining bar structure is substantially centered between opposed ends of the retaining bar attached to the base.

12. The reamer of claim 11 wherein the central retaining bar structure comprises opposed first and second radiused sides extending beyond respective planes of the first and second retaining bar sides, the opposed first and second radiused sides being aligned with each other along a perpendicular axis bisecting a longitudinal axis of the retaining bar.

13. The reamer of claim 10 wherein the shaft engagement portion comprises a cross bar.

14. The reamer of claim 1 wherein first ends of the respective first and second reamer blades reside adjacent to the lower shell edge diametrically opposite each other.

15. The reamer of claim 1 wherein second ends of the respective first and second reamer blades reside at the first imaginary bisecting plane.

16. The reamer of claim 1 wherein a central opening extends through the shell at the apex.

17. The reamer of claim 1 further comprising:
a) a third slit through the shell thickness, the third slit extending from at or adjacent to the lower shell edge and toward the second imaginary bisecting plane, wherein the third slit is spaced clockwise from the first imaginary bisecting plane with respect to a view looking along the rotational axis toward the lower shell edge;
b) a fourth slit through the shell thickness, the fourth slit extending from at or adjacent to the lower shell edge and toward the second imaginary bisecting plane, wherein the third slit is spaced clockwise from the first imaginary bisecting plane with respect to the rotational axis, but on an opposite side thereof with respect to the third slit; and
c) third and fourth reamer blades, each blade comprising a blade body extending to a cutting portion, the third and fourth blades received in the respective third and fourth slits with their cutting portions comprising a plurality of third and fourth cutting teeth spaced outwardly from the exterior shell surface.

18. A reamer, comprising:
a) a shell comprising a shell sidewall of at least a portion of a hemisphere, the shell sidewall having a shell thickness extending from an exterior surface to an interior surface, the interior surface extending from an apex to a lower shell, edge, the shell being detachably connectable to a reamer shaft for rotational movement about a rotational axis that extends through the apex and is aligned perpendicular to an imaginary edge plane at the lower shell edge, and wherein an imaginary bisecting plane intersects the rotational, axis and the imaginary edge plane, thereby bisecting the reamer body into two equal halves; and
b) at least one reamer blade removably supported by the shell sidewall, the blade comprising a blade body that extends from a proximal blade portion to a distal cutting portion, the blade body having a blade body thickness that extends between opposed first and second blade body sidewalls, the distal cutting portion comprising a plurality of cutting teeth spaced apart from each other and facing inwardly toward the rotational axis from the shell interior surface, wherein each tooth of the plurality of cutting teeth has a cutting edge that resides along the imaginary bisecting plane at a blade offset that extends between the imaginary bisecting plane and an imaginary centerline that extends between the opposed first and second blade body sidewalls parallel to the bisecting plane;
c) wherein rotation of the reamer body against bone and tissue causes the bone and tissue to be cut.

19. The reamer of claim 18 wherein with the at least one reamer blade supported by the shell sidewall, an imaginary cutting plane extends along the blade sidewall of the distal cutting portion through the cutting edge of each of the cutting teeth, and wherein a rake angle extends between the imaginary bisecting plane and the imaginary cutting plane.

20. The reamer of claim 18 wherein the proximal blade portion is positionable within a groove having a first groove end spaced from a second groove end, the groove comprising opposed groove sidewalls that extend outwardly from the shell interior surface toward the rotational axis, and wherein the proximal blade portion is removably positionable between the opposed groove sidewalls and between the first and second groove ends.

21. The reamer of claim 20 wherein the first groove end extends towards the apex and the second groove end is at or adjacent to the lower shell edge.

22. The reamer of claim 20 wherein the first groove end resides at the apex and the second groove end extends towards the lower shell edge.

23. The reamer of claim 18 wherein the proximal blade portion opposite the distal cutting portion is removably positionable within a groove that extends at least part-way through the shell thickness.

24. The reamer of claim 18 wherein at least a first opening extends through the shell thickness to provide a passageway for tissue to pass therethrough.

25. The reamer of claim 18 wherein a shaft engagement portion configured for detachable connection to a source of rotary drive motion is connected to the shell at or adjacent to the lower shell edge.

26. The reamer of claim 25 wherein the shaft engagement portion comprises a retaining bar with spaced apart first and second retaining bar sides extending to a base, and wherein a central retaining bar structure is substantially centered between opposed ends of the retaining bar attached to the base.

27. The reamer of claim 26 wherein the central retaining bar structure comprises opposed first and second radiused sides extending beyond respective planes of the first and second retaining bar sides, the opposed first and second radiused sides being aligned with each other along a perpendicular axis bisecting a longitudinal axis of the retaining bar.

28. The reamer of claim 25 wherein the shaft engagement portion comprises a cross bar.

29. The reamer of claim 18 wherein each of the plurality of cutting teeth comprises a relief surface provided at a trailing surface that resides between the opposed first and second blade sidewalls at the distal blade portion.

30. A reamer, comprising:
a) a reamer body connectable to a reamer shaft, the reamer body comprising a shell sidewall of at least a portion of a hemisphere, the shell sidewall having a shell thickness extending from an exterior surface to an interior surface, the interior surface extending from an apex to a lower shell edge, the shell being rotatable about a rotational axis that extends through the reamer body apex and is aligned perpendicular to the lower shell edge; and b) a shaft engagement portion connected to the exterior shell surface at or adjacent to the apex, wherein the shaft engagement portion comprises:
  i) a retaining bar with spaced apart first and second retaining bar sides extending to a base, and wherein a central retaining bar structure is substantially centered between opposed ends of the retaining bar attached to the base, or
  ii) a cross bar;
c) at least one reamer blade supported by the shell sidewall, the blade comprising a blade body having a blade thickness that extends to a cutting portion, the cutting portion comprising a plurality of cutting teeth spaced apart from each other and facing inwardly toward the rotational axis, wherein each tooth of the plurality of cutting teeth has a cutting edge;
d) wherein rotation of the reamer body against bone and tissue causes bone and tissue to be cut.

31. The reamer of claim 30 wherein the central retaining bar structure comprises opposed first and second radiused sides extending beyond respective planes of the first and second retaining bar sides, the opposed first and second radiused sides being aligned with each other along a perpendicular axis bisecting a longitudinal axis of the retaining bar.

32. The reamer of claim 30 wherein a blade proximal end residing opposite the cutting portion is positionable within a groove having opposed groove sidewalls that extend outwardly from the shell interior surface toward the rotational axis, the blade proximal end being positioned between the groove sidewalls.

33. The reamer of claim 30 wherein a blade body end surface residing opposite the cutting portion is positionable within a groove that extends at least part-way into the shell sidewall thickness.

34. The reamer of claim 30 wherein with the at least one reamer blade supported by the shell sidewall, an imaginary cutting plane extends along the blade sidewall of the distal cutting portion through the cutting edge of each of the plurality of cutting teeth, and wherein a rake angle extends between the imaginary bisecting plane and the imaginary cutting plane of the shell.

35. The reamer of claim 34 wherein the cutting edge resides at a blade offset that extends between the bisecting plane and an exterior surface of the blade body parallel to the blade thickness.

36. A reamer, comprising:
a) a shell, comprising:
  i) a shell sidewall having a convex exterior surface spaced from an interior surface by a shell thickness, wherein the shell extends from an apex to a lower shell edge, the shell being detachably connectable to a reamer shaft for rotational movement about a rotational axis that extends through the apex and is aligned perpendicular to an imaginary edge plane at the lower shell edge, and wherein a first imaginary bisecting plane and a second imaginary bisecting plane intersect the rotational axis and the imaginary edge plane offset 90° from each other;
  ii) a first slit through the shell thickness, the first slit extending from at or adjacent to the lower shell edge and toward the first imaginary bisecting plane, wherein the first slit is spaced clockwise from the second imaginary bisecting plane with respect to a view looking along the rotational axis toward the lower shell edge;
  iii) a second slit through the shell thickness, the second slit extending from at or adjacent to the lower shell edge and toward the first imaginary bisecting plane, wherein the second slit is spaced clockwise from the second imaginary bisecting plane with respect to the rotational axis, but on an opposite side thereof with respect to the first slit;
  iv) a third slit through the shell thickness, the third slit extending from at or adjacent to the lower shell edge and toward the second imaginary bisecting plane, wherein the fourth slit is spaced clockwise from the first imaginary bisecting plane with respect to a view looking along the rotational axis toward the lower shell edge; and
  v) a fourth slit through the shell thickness, the fourth slit extending from at or adjacent to the lower shell edge and toward the second imaginary bisecting plane, wherein the fourth slit, is spaced clockwise from the first imaginary bisecting plane with respect to the rotational axis, but on an opposite side thereof with respect to the third slit,
  vi) wherein the first, second, third and fourth slits are formed from opposed sidewalls that extend from the shell interior surface toward the rotational axis; and
b) a first reamer blade, a second reamer blade, a third reamer blade and a fourth reamer blade, each blade comprising a blade sidewall extending from a proximal blade portion to a distal cutting portion, wherein the first, second, third and fourth blades are removably positionable between the opposed sidewalls comprising the respective first, second, third and fourth slits with their distal cutting portions comprising a plurality of first, second, third and fourth cutting teeth extending outwardly from the exterior shell surface.

37. A reamer assembly, comprising:
a) a shell, comprising:
  i) a shell, sidewall having a convex exterior surface spaced from an interior surface by a shell thickness, wherein the shell extends from an apex to a lower shell edge, the shell being detachably connectable to a reamer shaft for rotational movement about a rotational axis that extends through the apex and is aligned perpendicular to an imaginary edge plane at the lower shell edge, and wherein a first imaginary bisecting plane and a second imaginary bisecting plane intersect the rotational axis and the imaginary edge plane offset 90° from each other;
  ii) a first slit through the shell thickness, the first slit extending from at or adjacent to the lower shell edge and toward the first imaginary bisecting plane, wherein the first slit is spaced clockwise from the second imaginary bisecting plane with respect to a view looking along the rotational axis toward the lower shell edge; and
  iii) a second slit through the shell thickness, the second slit extending from at or adjacent to the lower shell edge and toward the first imaginary bisecting plane, wherein the second slit is spaced clockwise from the second imaginary bisecting plane with respect to the rotational axis, but on an opposite side thereof with respect to the first slit;
b) a first reamer blade and a second reamer blade, each blade comprising:
  i) a blade sidewall extending from a proximal blade portion to a distal cutting portion, the first and second blades received in the respective first and second slits with their respective distal cutting portions comprising a plurality of first and second cutting teeth extending outwardly from the exterior shell surface, ii) wherein tabs of the respective first and second reamer blades extend distally beyond the lower shell edge with respect to the apex; and c) an adaptor, comprising:
i) an annular adaptor sidewall having a height extending from an upper surface to a lower portion, wherein the upper adaptor surface is configured for supporting contact of the shell; and
ii) a first slot and a second slot, both slots formed from opposed slot sidewalls that extend inwardly from the adaptor sidewall toward the rotational axis with the shell supported on the adaptor,
iii) wherein with the first and second blades received in the respective first and second slots of the shell supported on the adaptor, the first and second tabs are received in the first and second adaptor slots.

38. The reamer assembly of claim 37 wherein the adaptor is separable from the shell so that the first and second reamer blades are removable from the first and second slits and replaceable with a second pair of first and second blades received therein.

39. The reamer assembly of claim 37 wherein the first and second blades are diametrically opposite each other.

40. A reamer, comprising:
a) a shell, comprising:
i) a shell sidewall having a convex interior surface spaced from an exterior surface by a shell thickness, wherein the shell extends from an apex of the interior surface to a lower shell edge, the shell being detachably connectable to a reamer shaft for rotational movement about a rotational axis that extends through the apex and is aligned perpendicular to an imaginary edge plane at the lower shell edge, and wherein a first imaginary bisecting plane and a second imaginary bisecting plane intersect the rotational axis and the imaginary edge plane offset 90° from each other;
ii) a first slot extending from at or adjacent to the lower shell edge and toward the first imaginary bisecting plane, wherein the first slot is spaced clockwise from the second imaginary bisecting plane with respect to a view looking along the rotational axis toward the lower shell edge; and
iii) a second slot extending from at or adjacent to the lower shell edge and toward the first imaginary bisecting plane, wherein the second slot is spaced clockwise from the second imaginary bisecting plane with respect to the rotational axis, but on an opposite side thereof with respect to the first slot; and b) a first reamer blade and a second reamer blade, each blade comprising a blade sidewall extending from a proximal blade portion to a distal cutting portion, the first and second blades received in the respective first and second slots with their respective distal cutting portions comprising a plurality of first and second cutting teeth extending inwardly from the interior shell, surface and toward the rotational axis.

41. The reamer of claim 40 further comprising:
a) a third slot extending from at or adjacent to the lower shell edge and toward the second imaginary bisecting plane, wherein the third slot is spaced clockwise from the first imaginary bisecting plane with respect to a view looking along the rotational axis toward the lower shell edge;
b) a fourth slot extending from at or adjacent to the lower shell edge and toward the second imaginary bisecting plane, wherein the third slot is spaced clockwise from the first imaginary bisecting plane with respect to the rotational axis, but on an opposite side thereof with respect to the third slot; and
c) third and fourth reamer blades, each blade comprising a blade body extending to a cutting portion, the third and fourth blades received in the respective third and fourth slots with their cutting portions comprising a plurality of third and fourth cutting teeth spaced outwardly from the interior shell surface and toward the rotational axis.

* * * * *

UNITED STATES PATENT AND TRADEMARK OFFICE
CERTIFICATE OF CORRECTION

PATENT NO. : 9,011,442 B2
APPLICATION NO. : 13/355973
DATED : April 21, 2015
INVENTOR(S) : Victor Page 1 of 1

It is certified that error appears in the above-identified patent and that said Letters Patent is hereby corrected as shown below:

In the claims

Column 11, line 56 Claim 18, after "rotational" delete ","

Column 14, line 19 Claim 36, delete "fourth" and insert --third--

Signed and Sealed this
Tenth Day of May, 2016

Michelle K. Lee
*Director of the United States Patent and Trademark Office*